United States Patent
Kannt et al.

(10) Patent No.: US 7,279,286 B2
(45) Date of Patent: Oct. 9, 2007

(54) HIGH-THROUGHPUT-ASSAY WITH HIGH SENSITIVITY FOR MEASURING OF THE ACTIVITY OF β-ADRENERGIC RECEPTOR KINASE AND FOR DETERMINING THE IMPACT OF TEST SUBSTANCES ON SUCH ACTIVITY

(75) Inventors: Aimo Kannt, Frankfurt (DE); Antje Pommereau, Otterberg (DE); Harald Thuering, Frankfurt (DE); Jochen Huber, Maxdorf (DE); Martin Oppermann, Goettingen (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 41 days.

(21) Appl. No.: 10/931,161

(22) Filed: Aug. 31, 2004

(65) Prior Publication Data

US 2005/0059098 A1  Mar. 17, 2005

Related U.S. Application Data

(60) Provisional application No. 60/538,908, filed on Jan. 23, 2004.

(30) Foreign Application Priority Data

Sep. 11, 2003  (EP) .................................. 03020429

(51) Int. Cl.
G01N 33/53 (2006.01)
(52) U.S. Cl. ........................................ 435/7.1; 435/7.72
(58) Field of Classification Search .................... None
See application file for complete search history.

(56) References Cited

U.S. PATENT DOCUMENTS 6,203,994 B1 * 3/2001 Epps et al. .................. 435/7.1

FOREIGN PATENT DOCUMENTS

WO  WO 02/22882  3/2002

OTHER PUBLICATIONS

Gray et al. Nonradioactive Methods for the Assay of Phosphoinositide 3-Kinases and Phosphoinositide Phosphatases and Selective Detection of Signaling Lipids in Cell and Tissue Extracts; Analytical Biochemistry, vol. 313 (2003) pp. 234-345.*
AlphaScreen Technical Support: AlphaScreen Technology Application Note ASC-001; Principles of Alphascreen (2001), www.packardbioscience.com.*
B. Pollok-Kopp et al., Analysis of Ligand-simulated CC Chemokine Receptor 5 (CCR5) Phosphorylation in Intact Cells Using Phosphite-specific Antibodies, Journal of Biological Chemistry, vol. 278, No. 4, Jan. 24, 2003, pp. 2190-2198.
C. Bieri et al., Micropatterned immobilization of a G protein-coupled receptor and direct detection of G protein activation, Nature Biology, vol. 17, Nov. 1999, pp. 1105-1108.
J. Peppard et al., Development of a High-Throughput Assay for Inhibitors of Aggrecan Cleavage Using Luminescent Oxygen Channeling (AlphaScreen), Journal of Biomolecular Screening, vol. 8, No. 2, 2003, pp. 149-156.
M.A. Sills et al., Comparison of Assay Technologies for a Tyrosine Kinase Assay Generates Different Results in High Throughput Screening, Journal of Biomolecular Screening, vol. 7, No. 3, 2002, pp. 191-214.
N. Rouleau et al., Development of a Versatile Platform for Nuclear Receptor Screening Using AlphaScreen, Journal of Biomolecular Screening, vol. 8, No. 2, 2003, pp. 191-197.
X. Wu et al., Comparison of Assay Technologies for a Nuclear Receptor Assay Screen Reveals Differences in the Sets of Identified Functional Antagonists, Journal of Biomolecular Screening, vol. 8, No. 4, 2003, pp. 381-392.
Y. Li et al., Homogeneous assays for adenosine 5'-monophosphate-activated protein kinase, Analytical Biochemistry, vol. 321, 2003, pp. 151-156.

* cited by examiner

*Primary Examiner*—Jon Weber
*Assistant Examiner*—Paul Martin
(74) *Attorney, Agent, or Firm*—Karen I. Krupen (57) ABSTRACT

The present invention relates to an assay for determining the activity of a G-Protein-Coupled Receptor specific protein kinase by means of an amplified luminescent proximity homo homogenous assay.

19 Claims, 5 Drawing Sheets

APERASSVYTRSTGEQEISVGL

Fig. 6

MADLEAVLAD VSYLMAMEKS KATPAARASK KILLPEPSIR SVMQKYLEDR GEVTFEKIFS
QKLGYLLFRD FCLNHLEEAR PLVEFYEEIK KYEKLETEEE RVARSREIFD SYIMKELLAC
SHPFSKSATE HVQGHLGKKQ VPPDLFQPYI EEICQNLRGD VFQKFIESDK FTRFCQWKNV
ELNIHLTMND FSVHRIIGRG GFGEVYGCRK RDTGKMYAMK CLDKKRIKMK QGETLALNER
IMLSLVSTGD CPFIVCMSYA FHTPDKLSFI LDLMNGGDLH YHLSQHGVFS EADMRFYAAE
IILGLEHMHN RFVVYRDLKP ANILLDEHGH VRISDLGLAC DFSKKKPHAS VGTHGYMAPE
VLQKGVAYDS SADWFSLGCM LFKLLRGHSP FRQHKTKDKH EIDRMTLTMA VELPDSFSPE
LHSLLEGLLQ RDVNRRLGCL GRGAQEVKES PFFRSLDWQM VFLQRYPPPL IPPRGEVNAA
DAFDIGSFDE EDTKGIKLLD SDQELYRNFP LTISERWQQE VAETVFDTIN AETDRLEARK
KAKNKQLGHE EDYALGKDCI MHGYMSKMGN PFLTQWQRRY FYLFPNRLEW RGEGEAPQSL
LTMEEIQSVE ETQIKERKCL LLKIRGGKQF ILQCDSDPEL VQWKKELRDA YREAQQLVQR
VPKMKNKPRS PVVELSKVPL VQRGSANGL

HIGH-THROUGHPUT-ASSAY WITH HIGH SENSITIVITY FOR MEASURING OF THE ACTIVITY OF β-ADRENERGIC RECEPTOR KINASE AND FOR DETERMINING THE IMPACT OF TEST SUBSTANCES ON SUCH ACTIVITY

CROSS REFERENCE TO RELATED APPLICATIONS

This Application claims benefit to U.S. Provisional Application 60/538,908 filed Jan. 23, 2004 and European Patent Office (EPO) 03020429.1 filed Sep. 11, 2003.

FIELD OF THE INVENTION

The present invention relates to a GPCR specific protein kinase assay by means of head linked substrate molecules.

G-protein-coupled receptors (GPCRs) are a very large protein family with thousands of known members. GPCRs share limited amino acid sequence homology and a similar protein topology with an N-terminal extracellular segment, seven hydrophobic membrane spanning α-helics and a C-terminal cytoplasmic region. Increased activity of the human heart is mediated by β-adrenergic receptors (β-AR), which are GPCRs responding to adrenergic sympathetic stimulation. Decreased cardiac activity is mediated by the cholinergic parasympathetic system working through muscarinic acetylcholine GPCRs. Cardiac β-AR consists of both the $β_1$ and $β_2$ subtypes, and in the human heart, as in most mammals, the $β_1$, is predominant. The two proteins are rather similar in protein sequence, though the $β_1$ is significantly larger due to a larger N-terminal extracellular region and a larger C3 cytoplasmic loop.

These β-AR interact with heterotrimeric guanine nucleotide binding regulatory proteins, usually known as trimeric G-proteins. Trimeric G-proteins consist of an α, β and γ subunit, each represented by several different genes in humans.

Six mammalian cDNAs encoding members of the GRK (G Protein Specific Receptor Kinase) subfamily of serine/threonine kinases (EC. 2.7.1-) have been identified to date: GRK1 (rhodopsin kinase); GRK2 (β-adrenergic receptor kinase-1); GRK3 (B-adrenergic receptor kinase-2); GRK4; GRK5; and GRK6. With the exception of GRK1 which is found almost exclusively in retina and GRK4 which is expressed at significant levels only in testes, GRKs are ubiquitously expressed. GRK4 is the only member of this family shown to undergo alternative splicing. Four splice variants exist, with the alternatively spliced exons occurring in the amino and carboxyl termini.

Evolutionary Conservation among GRKs isolated from nematodes, insects, and mammals emphasizes their biological importance. GPRK1 and wj283.2 encode, respectively, Drosophila and Caenorhabditid elegans proteins with 62% and 51% homology to bovine GRK2. Similarly, GPRK2 and f19c6.1 encode Drosophila and C. elegans proteins with 50-53% homology to bovine GRK5. Among the six mammalian GRKs, the amino acid sequence similarity is 53-93%, with GRK1 and GRK2 being the most divergent.

GRKs are most closely related to the PKC and cAMP-dependent protein kinase families (PKAs). Based on sequence and functional similarities, the GRK family has been divided into three subfamilies: [a] GRK1, [b] GRK2 or β-adrenergic receptor kinase (β-ARK); (GRK2 and GRK3), and [c] GRK4 (GRK4, GRK5, and GRK6). Members of the GRK2 subfamily share approximately 84% sequence similarity, and members of the GRK4 subfamily share approximately 70% sequence similarity.

In the failing human heart, cardiac β-adrenergic receptors are stimulated by an increased release of catecholamines from the sympathetic nerves to maintain cardiac output and blood pressure. This increase in β-adrenergic receptor agonists leads to a downregulation of the receptor (and thus to a lower receptor density) and a receptor desensitization mediated by overexpression of βARK. Thus, treatment with βARK inhibitors may be of benefit for the preservation of myocardial β-adrenergic receptor signaling and may delay the development of heart failure after myocardial infarction.

Assays for testing GRK are known from the state of the art. For example in "Haga et al., 1998, GPT-binding-protein-coupled receptor kinase 2 (GRC2) binds and phosphorylates tubulin, Eur. J. Biochem. 255, 363-368" an assay for GRK2 has been described by means of radioactively labeled substrate molecules.

The AlphaScreen technology is widely used for testing of different types of enzymes. AlphaScreen Assays of different specificity are commercially available e.g. from Perkin-Elmer.

AlphaScreen is a bead based non-radioactive Amplified Luminescent Proximity Homogeneous Assay. When a biological interaction brings the beads together, a cascade of chemical reactions act to produce a greatly amplified signal. On laser excitation, a photosensitizer in the Donor bead converts ambient oxygen to a more excited singlet state. The singlet state oxygen molecules diffuse across to react with a thioxene derivative in the Acceptor bead, generating chemiluminescence at 370 nm that further activates fluorophores contained in the same bead. The fluorophores subsequently emit light at 520-620 nm.

In the absence of a specific biological interaction, the single state oxygen molecules produced by the Donor bead go undetected without the close proximity of the Acceptor bead. As a result no signal is produced.

BRIEF SUMMARY OF THE INVENTION

AlphaScreen provides a highly versatile, sensitive, time-resolved, homogeneous and miniaturizable means to efficiently perform assay development and HTS resulting in higher throughput at lower costs.

The lifetime of singlet oxygen in solution is about 4 µs which corresponds to a diffusion distance of approximately 200 nm. Thus, a signal is only generated when donor and acceptor beads are in close proximity to each other.

In the βARK inhibition experiment biotinylated hunian CC ehemokine receptor 5, herein abbreviated CCR5 peptide (Seq. ID No. 1) is phosphorylated by the kinase. The phosphorylated serine is recognized by a specific antibody which, in turn, is bound to protein A coupled acceptor beads. The biotinylated N-terminus of the CCR5 peptide is coupled to streptavidin-coated donor heads. Thus, in the absence of inhibitors an AlphaScreen signal is detected that decreases when the enzymatic activity in inhibited.

SUMMARY OF THE INVENTION

The assay of the invention in particular the test of βARK activity by means of the AlphaScreen technology design is new. Compared to the state of the art determination of the βARK activity is much more sensitive since the change of substrate phosphorylation is detectable within the nM-range.

Furthermore the assay is homogenous which means that additional washing steps or immobilization of reactants are easily avoidable since the reaction is performed by means of solid phases. The assay is suitable for miniaturization which allows the use in high throughput screening by laboratory robots. A further advantage is that the substrate does not need to be modified by covalent binding to fluorescence dyes.

DETAILED DESCRIPTION OF THE INVENTION

Figure 1:
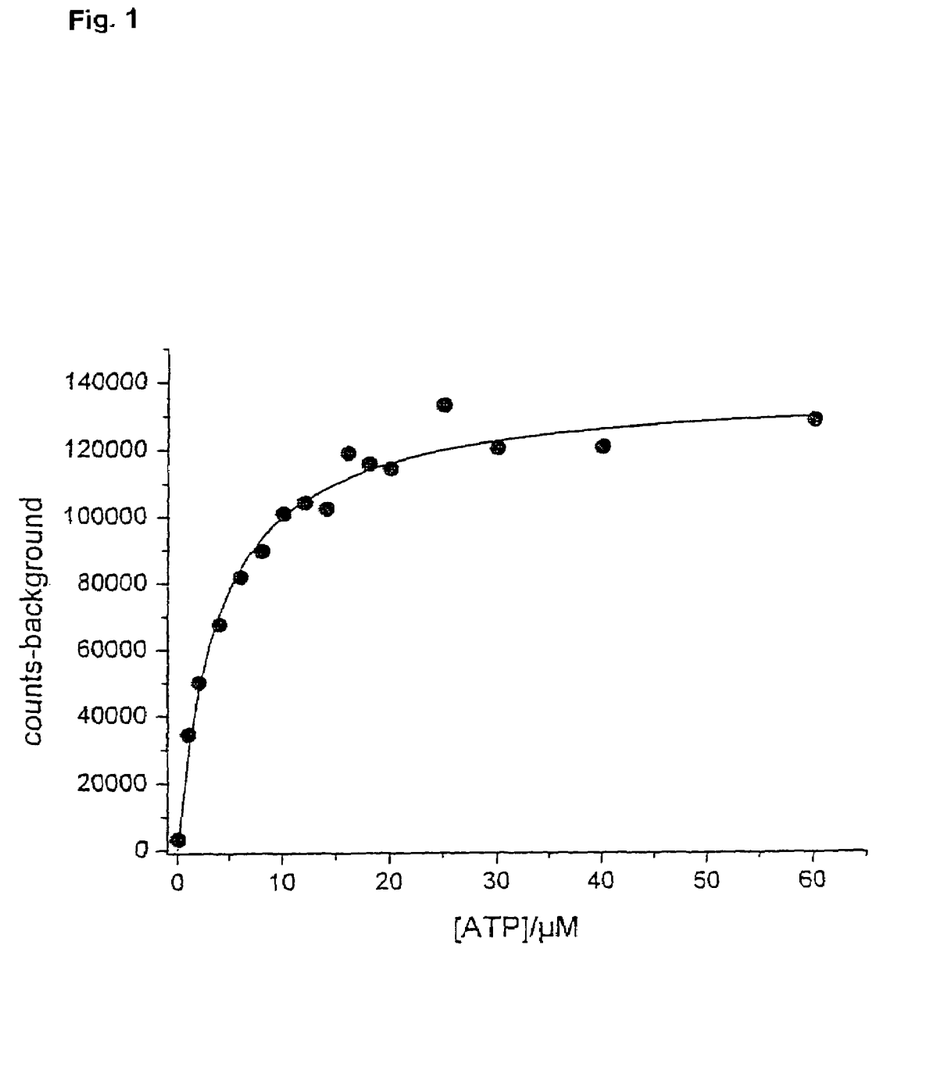
FIG. 1 Assay validation; ATP dependence; the apparent Km value was determined at 4 µM FIG. 2 Stability of the reaction mix; reagents are stable for more than 3 hours.
Figure 2:
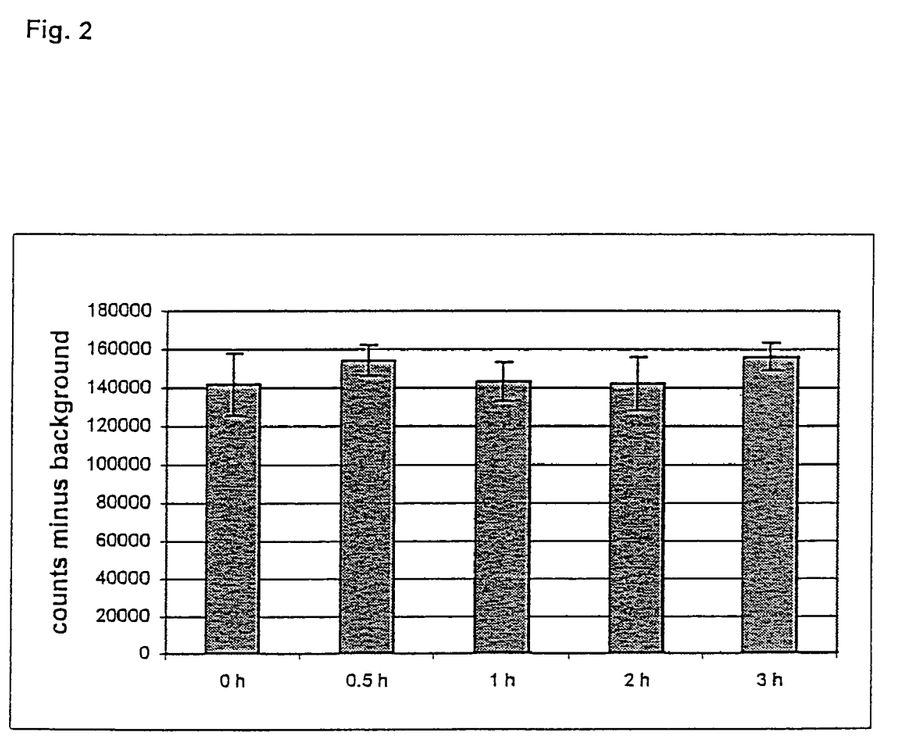
Figure 3:
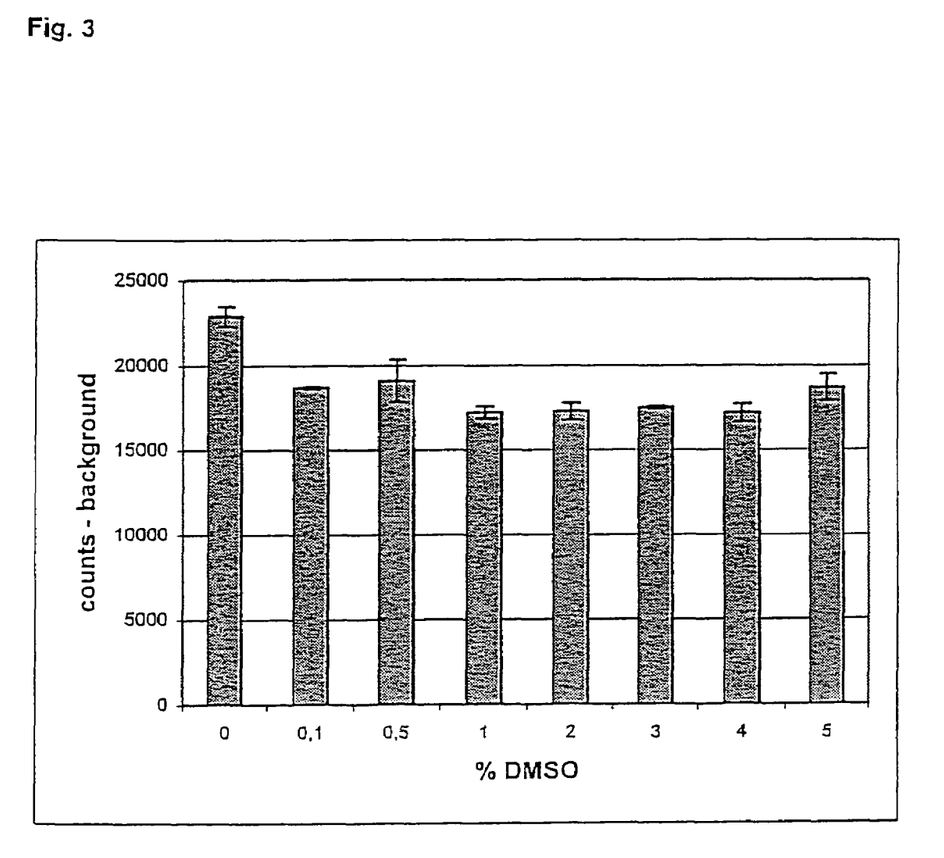
FIG. 3 DMSO dependence of the assay; the assay tolerates up to 5% DMSO
Figure 4:
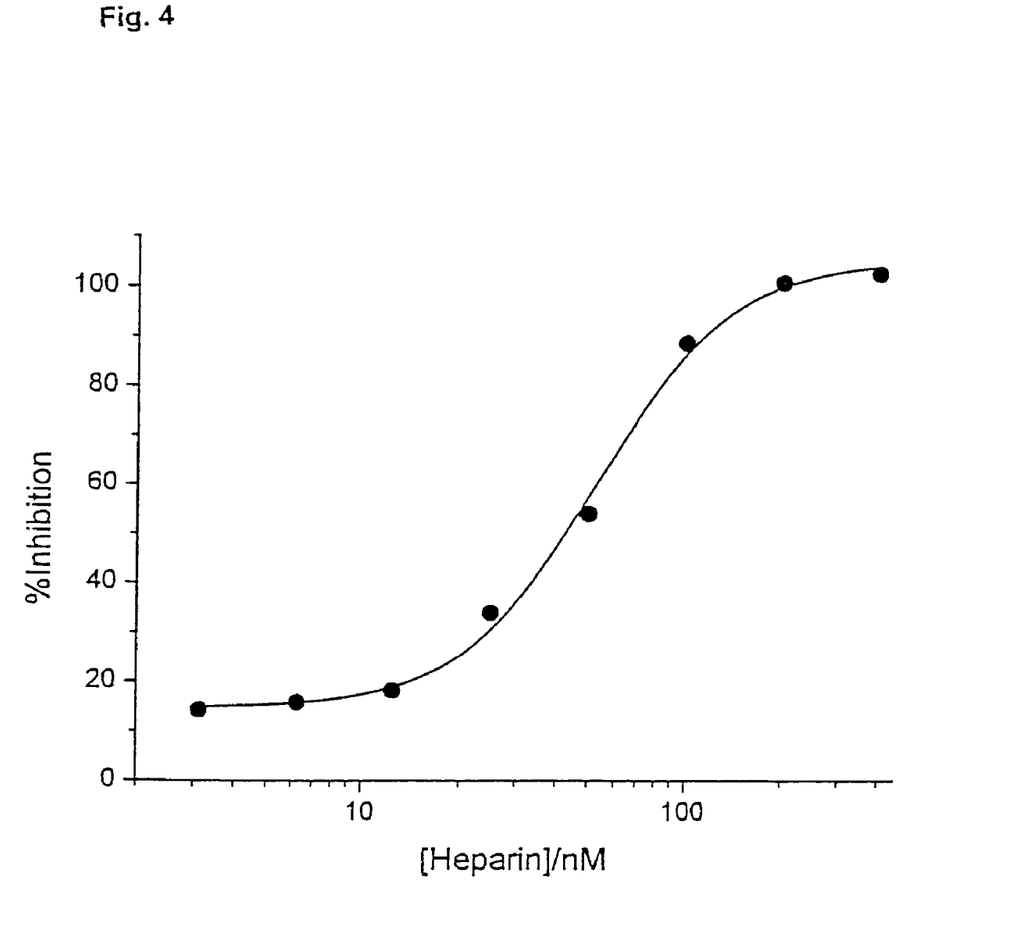
FIG. 4 Dose-response curve for heparin; the IC50 was determined as 50 nM
Figure 5:
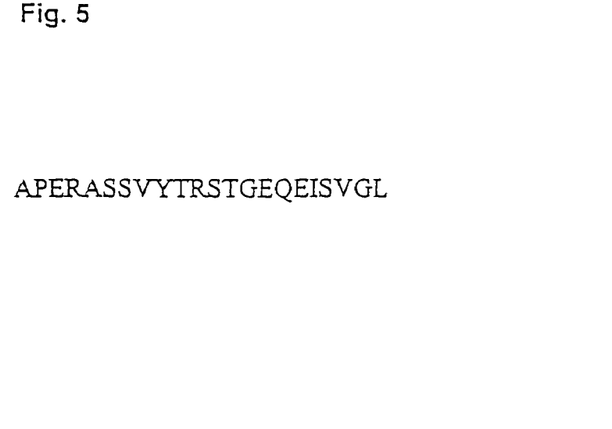
FIG. 5 Amino acid sequence according to Seq. Id No. 1
Figure 6:
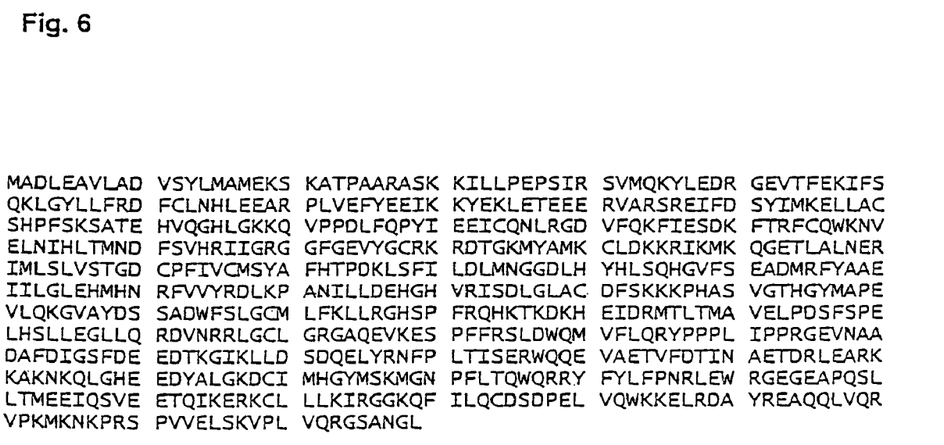
FIG. 6 Amino acid sequence including the βARK-1 Sequence according Seq. ID No. 2

The invention comprises in one embodiment a

Method for Detecting the Phosphorylation of a Substrate Molecule by a Protein Kinase Wherein
 a] at least one protein kinase is provided,
 b] at least one substrate molecule of the protein kinase of a] is provided,
 c] at least one donor component which is able to bind to the substrate molecule from b] and which emits a signal after the donor component was irradiated by a light source,
 d] at least one acceptor component which is able to recognize the substrate of b] in case it had been phosphorylated and which acceptor component is able to receive a signal in the form of an electromagnetic radiation is provided,
 e] the protein kinase from a], the substrate molecule from b], the donor component from c] and the acceptor component from d] are brought in contact,
 f] the mixture of e] is irradiated with a light source in such a way that the donor component of c] is excited,
 g] the electromagnetic radiation which is emitted by the mixture of e] is detected.

A substrate molecule shall mean any chemical compound which is phosphorylatable by a protein kinase. A substrate molecule consists preferably of a peptide or a protein. A substrate molecule may consist of a G-Protein coupled Receptor or a member of a signaling cascade.

A donor component is able by means of a donor compound to emit a signal after irradiation by a light source.

The signal may consist of an electromagnetic radiation which is characterized by a specific wavelength or may consist of an atom or of a molecule or another type of output.

An acceptor component is able to emit electromagnetic radiation upon having received the signal from the donor component. This electromagnetic radiation is characterized by its specific wavelength. It can be detected by means of an analysis apparatus as e.g. by a spectrometer.

In further embodiments of the invention the substrate molecule can be linked to an antibody which is able to bind to the donor component or the donor component is linked to an antibody which is able to bind to the substrate molecule.

In a further preferred embodiment of the invention the substrate molecule can be linked to a first antibody and the donor component can be linked to a second antibody wherein either the first antibody is able to bind to the second antibody or the second antibody is able to bind to the first antibody.

The linking of a compound to one or several other compounds shall mean that the connection between these two compounds occurs permanently. The linking is realized e.g. by covalent chemical bondages, or electrostatic forces as mediated by ionized molecules or by other means.

The binding of a compound to one or several other compounds shall start from a non-binding stage, then continue to the contracting of the two compounds after finally forming a strong bondage between the said compounds. This bondage may be characterized by binding constants which are preferably within range of $5 \times 10^{-9}$ to $5 \cdot 10^{-7}$M.

In a further embodiment of the method the substrate component is linked to a biotin molecule and the donor component is linked to streptavidin or the substrate component is linked to streptavidin and the donor compound is linked to biotin.

Biotin and streptavidin can bind to each other. Other chemical groups linked to the substrate component or donor component which are able to bind to each other comprise e.g. DNA and RNA binding proteins and the corresponding polynucleotide binding motifs.

The Protein kinase is e.g. the beta-Adrenerge-Receptor-Kinase1 or the G-Protein-Coupled-Receptor-Kinase2.

The substrate can consist of a G-protein coupled Receptor or of the muscarinic Acetylcholine-Receptor or an adrenergic alpha 2 Receptor.

In a further embodiment of the invention the acceptor component is linked to at least one antibody which specifically binds to the substrate of b] in case this substrate had been phosphorylated. Such an antibody is e.g. the monoclonal antibody E11/19. Manufacturing of this antibody was described in "Pollak-Kapp. et al., J. Biol. Chem. (2003), 278, 2190-2198".

The electromagnetic radiation which is emitted by the mixture according to g] of the method of the invention for detecting the phosphorylation of a substrate molecule can be fluorescence radiation. The electromagnetic radiation according to g] may be detected, for example, with the aid of a photomultiplier.

The light source for irradiation of the mixture according to f] of the method of the invention for detecting the phosphorylation of a substrate molecule can be a laser or a lamp.

The signal from the donor component to the acceptor component can be transferred preferably by emissionless energy transfer. This energy transfer can be a fluorescence resonance energy transfer.

In this case it is possible to carry out the method, for example, in such a way that the at least one compound or group of compounds according to b] (donor group) comprises a europium salt-containing compound and that the at least one compound or group of compounds according to c] (acceptor group) may comprise allophycocyanine (Grepin et al. (2000), Drug Discovery Today 5, 212).

Alternatively, the donor and acceptor groups may be dyes suitable for emissionless energy transfer. It is furthermore possible to use all compounds known to the skilled worker which are suitable for emissionless energy transfer, in particular for fluorescence resonance energy transfer (see, for example, Pope et al. (1999), Drug Discovery Today 4, 350). In this embodiment, preference is given to choosing the binding components to be used in such a way that the distance between the donor and acceptor groups after binding is less than 10 nm, since an effective emissionless energy transfer is probably not possible at a larger distance.

The signal from the donor component to the acceptor component can be transferred via singlet oxygen.

In a further embodiment of the method of the invention for detecting the phosphorylation of a substrate molecule the donor component according to c] can comprise a compound which is able to convert triplet oxygen to singlet oxygen after excitation by a laser wherein the acceptor component according to d] comprises at least one first compound excitable by singlet oxygen and at least one second compound capable of absorbing in an emissionless manner and emitting in the form of fluorescence radiation the energy absorbed by the first compound.

The singlet oxygen formed may diffuse from the donor group to the acceptor group and react with the chemiluminescent substances present there. The energy released in the process is transferred to the fluorophores which finally emit the energy in the form of fluorescence radiation which can be detected using a photomultiplier. A precondition for a detectable signal is the spatial proximity of donor and acceptor beads, since singlet oxygen is unstable and decays in aqueous solution. Therefore, the binding components to be used in this method are chosen in such a way that, when the binding event occurs, the distance between the donor and acceptor groups is preferably less than 200 nm.

Particular preference is given in this embodiment to donor group and acceptor group localized on particles, the particles preferably having an average diameter of between 150 and 250 nm, particularly preferably of approximately 200 nm. The preferred use of the particles here is such that the final concentration of acceptor group-carrying particles is 1-40 µg/ml and the final concentration of acceptor group-carrying particles is 1-80 µg/ml. The binding capacity of the particles may be, for example, from approximately 0.1 nM to 1 nM per µm/ml particles.

Particular preference is given to using AlphaScreen beads from Perkin-Elmer Life Sciences as particles in the method. In this embodiment, the donor group is excited by irradiating at a wavelength of 680 nm, using a laser, and the radiation emitted by the acceptor group can be detected at a wavelength between 520 and 600 nm. According, it is possible, in this case, for the method to be carried out in such a way that donor and acceptor beads carrying donor and acceptor groups are introduced initially.

The donor and/or acceptor compound can consist of particles on which donor groups or acceptor groups are localized on. Such particles have preferably an average diameter of approximately 200 nm.

The method of the invention for detecting the phosphorylation of a substrate molecule may further comprise in another embodiment the steps of adding at least one test substance and observing how the test substance influences the activity of the protein kinase.

The method of the invention is in either case an HTS (high throughput screening)-capable method which may be carried out homogenously in the form of a one-step method. In a preferred embodiment, the method of the invention is carried out according to the "mix and measure" principle.

The HTS-capable assay systems of the invention are used here preferably for carrying out the above-described methods of the invention.

A particular characteristic feature of the methods of the invention is the possibility of monitoring the kinasing of the substrate in solution, since none of the reactants needs to be immobilized on a solid phase. Moreover, it is possible to measure the protein kinases from biological sources directly.

One may employ a reduced sample volume of the method of the invention compared to conventional methods. Thus it is possible to use volumes of less than 10 µl. Moreover, it is possible to use highly diluted solutions of the substrate of less than 1 nM, even less than 100 pM.

Fluorescence is, in theory, the most sensitive analytical technique. As many intra- and intermolecular processes are able to modulate the label emission, it was therefore under consideration very early on as a technique of choice for designing homogeneous assays. Polarization, quenching, time correlation, lifetime variation as well as fluorescence resonance energy transfer (FRET) have been applied to probing molecular interactions. Among these techniques, FRET is of particular interest.

However, severe limitations still remain for most of these applications, including low modulation range, interference from the assay medium (serum, biological fluid others), non specific interaction with media constituents, highly variable fluorescence background and light scattering from proteins, molecules and aggregates in the media.

For commonly known donor-acceptor pairs, the distance $R_0$ (for which transfer is 50% efficient) lies within the 1-7 nm range. Taking advantage of these properties, FRET was used as a spectroscopic ruler to reveal proximity relationships in biological macromolecules.

Since only a very few techniques allow such distance and interactions to be determined in solution, many domains of biology were explored with FRET, such as enzymatic activity, protein-DNA interactions, and cell surface lectin revealed receptor-ligand interactions. DNA hybridization has attracted much attention and is now becoming a field of investigation for FRET experiments, either for structural investigations, olinucleotide hybridizations or detection of gene translocation. Because the processes involved in FRET occur within distances characteristic of antigen antibody interactions, homogeneous fluoroimmunoassays have also been developed. More recently, FRET was used to monitor receptor oligomerisation, a key process in the cell signaling pathway.

In one embodiment the invention comprises an assay for determining the activity of a G-Protein-Coupled-Receptor specific protein kinase wherein a] a protein kinase is provided, b] a donor bead, which streptavidin is linked to, of an amplified luminescent proximity homogenous assay is provided, c] a substrate molecule, which a biotin molecule is covalently linked to, of the protein kinase from a] is provided, which substrate molecule is phosphorylatable by the protein kinase from a], d] an antibody is provided that specifically recognizes the phosphorylated substrate molecule from c]

e] an acceptor bead, which is or can be linked to the antibody from d] by means of, e.g., protein A or a suitable secondary antibody, of an amplified luminescent proximity homogenous assay is provided, f] the protein kinase from a], the donor bead from b], the substrate molecule from c], the antibody from d] and the acceptor bead from e] are incubated simultaneously, g] the emission of light is determined at one or several wave lengths between 520 and 620 mm, h] the activity of the protein kinase from a] is calculated from emission of light accordingly to g] wherein the maximum emission of light shall indicate the standard activity of the protein kinase, i] possibly the activity of a second protein kinase, which is of the same type of species as the protein kinase from a] or which is of a different type of species as the protein kinase from a], is determined and calculated accordingly to steps a] to h] wherein the calculation accordingly to h] for the protein kinase from a] is taken as reference for comparing the activity of the second protein kinase thereby indicating a decrease of activity of the second protein kinase in case the emission of light of the second protein kinase is diminished when compared to the emission of light of the protein kinase from a].

In preferred embodiments of the assay for determining the activity of a G-Protein-Coupled-Receptor specific kinase as mentioned before the protein kinase according to a] is selected from the group of β-Adrenergic-Receptor-Kinase 1 (βARK1] or G-Protein-Coupled-Receptor 2 (GRK2].

In further embodiments of the assay for determining the activity of a G-Protein-Coupled-Receptor specific kinase as mentioned before the substrate according to c] consists preferably of a G-Protein-Coupled-Receptor which is selected from the group of a muscarinic Acetylcholine-Receptor or an adrenergic alpha 2 Receptor.

In additional embodiments of the assay for determining the activity of a G-Protein-Coupled-Receptor specific kinase as mentioned before the substrate according to c] consists preferably of a peptide being composed of between 10 and 50 amino acids or consists more preferably of a peptide being composed of an amino acid sequence of Seq. ID No. 1.

In a further preferred embodiment of the assay for determining the activity of a G-Protein-Coupled-Receptor specific kinase as mentioned before as antibody according to d] the monoclonal antibody E11/19 can be used. Manufacturing of such antibody was described in "Pollok-Kopp et al., J. Biol. Chem. 2003, 278, 2190-2198". Such antibody can be linked to the acceptor bead via protein A or a suitable secondary antibody.

In one embodiment the invention refers to a kit of parts, which kit of parts comprises
a] at least one protein kinase,
b] at least one donor bead, which streptavidin is linked to, of an amplified luminescent proximity homogenous assay,
c] at least one substrate molecule, which a biotin molecule is covalently linked to, of a protein kinase from a] which substrate molecule is phosphorylatable by a protein kinase from a],
d] an antibody is provided that specifically recognizes the phosphorylated substrate molecule from c]
e] at least one acceptor bead, which is or can be linked to the antibody from d] by means of, e.g., protein A or a suitable secondary antibody, of an amplified luminescent proximity homogenous assay is provided.

The components of the kit of parts may be used simultaneously or one after another in one combined or several distinguished use forms. A use form consists for example of an incubation approach including a vessel for incubation, a liquid for incubation and incubation conditions as temperature or time.

In preferred embodiments of the kit of parts as mentioned before the protein kinase according to a] is selected from the group of β-Adrenergic-Receptor-Kinase1 (βARK1] or G-Protein-Coupled-Receptor-Kinase2 (GRK2].

In further embodiments of the kit of parts as mentioned before the substrate according to c] consists preferably of a G-Protein-Coupled-Receptor or more preferably of a G-Protein-Coupled-Receptor which is selected from the group of a muscarinic Acetylcholine-Receptor or an adrenergic alpha2 Receptor.

In additional embodiments of the kit of parts as mentioned before the substrate according to c] consists preferably of a peptide being composed of between 10 and 50 amino acids or consists more preferably of a peptide being composed of an amino acid sequence of Seq. ID No. 1.

In further preferred embodiment of a kit of parts as mentioned before as antibody according to d] the monoclonal antibody E11/19 can be used. Such antibody can be linked to the acceptor bead via protein A or a suitable secondary antibody.

In one embodiment the invention comprises the manufacturing of a kit of parts which kit of parts has been described as mentioned before wherein
a] at least one protein kinase is provided,
b] at least one donor bead, which streptavidin is linked to, of an amplified luminescent proximity homogenous assay is provided,
c] at least one substrate molecule, which a biotin molecule is covalently linked to, of a protein kinase from a] which substrate molecule is phosphorylatable by a protein kinase from a], is provided,
d] an antibody is provided that specifically recognizes the phosphorylated substrate molecule from c]
e] at least one acceptor bead, which is or can be linked to the antibody from d] by means of, e.g., protein A or a suitable secondary antibody, of an amplified luminescent proximity homogenous assay is provided,
f] the components from a] to e] are packaged individually or combined in one or several containers,
g] at least one container from f] is possibly packaged into at least one second container,
h] at least one container from f] and/or g] is supplied with instructive material and/or labeled.

The kit of parts as described before can be used for determining the activity of a protein kinase and/or can be used in a screening process which may be organized as High-Throughput-Screening (HTS) for identifying a compound which increases the activity of a protein kinase and/or can be used for identifying a compound which decreases the activity of a protein kinase and/or can be used in a screening process which may be organized as High-Throughput-Screening (HTS] for identifying a compound which decreases the activity of a protein kinase.

In one embodiment the invention comprises a method for identifying a compound, which decreases the activity of a G-Protein-Coupled-Receptor specific protein kinase, wherein
a] a protein kinase is provided,
b] a donor bead, which streptavidin is linked to, of an amplified luminescent proximity homogenous assay is provided,
c] a substrate molecule, which a biotin molecule is covalently linked to, of the protein kinase from a] is provided, which substrate molecule is phosphorylatable by the protein kinase from a]
d] an antibody is provided that specifically recognizes the phosphorylated substrate molecule from c]
e] an acceptor bead, which is or can be linked to the antibody from d] by means of, e.g., protein A or a suitable secondary antibody, of an amplified luminescent proximity homogenous assay is provided,
f] a chemical compound is provided,
g] the protein kinase from a], the donor bead from b], the substrate molecule from c], the antibody from d], the acceptor bead from e] and the chemical compound from f] are incubated simultaneously, h] the emission of the light is determined at one or several wave lengths between 520 and 620 nm, i] the activity of the protein kinase from a] is calculated from emission of light accordingly to h] wherein the maximum emission of light shall indicate the standard activity of the protein kinase, j] the activity of the protein kinase as calculated accordingly to i] is set in relation to the result of a test wherein the protein kinase from a], the donor bead from b], the substrate molecule from c], the antibody from d] and the acceptor bead from e] are incubated simultaneously thereby indicating a decrease of the protein kinase if the activity of the protein kinase is diminished in case the protein kinase is incubated in presence of the chemical compound accordingly to f].

In preferred embodiments of a method for identifying a compound which decreases the activity of a G-Protein-Coupled-Receptor specific protein kinase as mentioned before the protein kinase according to a] is selected from the group of β-Adrenergic-Receptor-Kinase1 (βARK1] or G-Protein-Coupled-Receptor-Kinase2 (GRK2].

In further embodiments of a method for identifying a compound which decreases the activity of a G-Protein-Coupled-Receptor specific protein kinase as mentioned before the substrate according to c] consists preferably of a G-Protein-Coupled-Receptor or consists more preferably of a G-Protein-Coupled-Receptor which is selected from the group of a muscarinic Acetylcholine-Receptor or an adrenergic alpha 2-Receptor.

In additional embodiments of a method for identifying a compound, which decreases the activity a G-Protein-Coupled-Receptor specific protein kinase as mentioned before the substrate according to c] consists preferably of a peptide being composed of between 10 and 50 amino acids or consists more preferably of a peptide being composed of an amino acid sequence of Seq. ID No. 1.

In a further preferred embodiment of a method for identifying a compound, which decreases the activity of a G-Protein-Coupled-Receptor specific protein kinase as mentioned before as antibody according to d] the monoclonal antibody E11/19 can be used. Such antibody can be linked to the acceptor bead via protein A or a suitable secondary antibody.

In one embodiment the invention comprises a chemical compound having the ability to diminish the activity of a G-Protein-Coupled-Receptor specific kinase which is identified by a method for identifying a compound, which decreases the activity of a G-Protein-Coupled-Receptor as has been described in a former part of this invention. Such compound has preferably a mass of between 0, 1 to 50 kDa. Such compound is preferably selected from one of the following groups of a protein, an amino acid, a polysaccharide, a sugar, a polynucleotide, a nucleotide, a fatty acid containing compound, a fat, a fatty acid, a derivative of a fatty acid and or an aromatic carbon compound. Such a compound could be the component of a medicament besides pharmaceutically acceptable expedients for the treatment of a disease which is linked to a disabled phosphorylation of a G-Protein-Coupled-Receptor.

The invention comprises in one embodiment a peptide consisting of an amino acid sequence of Seq. ID No. 1. Such a peptide could be biotinylated. Synthesis of the peptide according to Seq. ID No. 1 carrying or lacking a Biotin-residue can be carried out by a peptide synthesis machine. Such synthesis machines are commercially available e.g. by Perkin Elmer.

The peptide according to Seq. ID No. 1 carrying or lacking a Biotin residue can be used as substrate molecule in a protein kinase test.

The invention concerns further the use of antibody E11/19 for detecting of a protein or peptide which is phosphorylated. This protein or peptide may encompass or consist of an amino acid according to Seq. ID No. 1.

The following chapters deal with general technical aspects of the invention.

Providing of a protein can be performed by a several step approach possibly including cloning of the corresponding gene of the protein in an appropriate expression vector, the transformation of e.g. bacterial cells, cultivation of such cells and expression of the said protein, harvesting of the cells from cultivation medium and the breakdown of the cells, and further isolation of the protein by e.g. ion exchange chromatography, size exclusion chromatography, high pressure liquid chromatography, affinity chromatography, polyacrylamide chromatography or other methods. The person skilled in the art will find appropriate methods for purification and handling of proteins in standard textbooks as in e.g. "Current Protocols in Protein Science—ISBN:0-471-11184-8 (eds: John E. Coligan, Ben M. Duan, Hidde L. Ploegh, David W. Speicher, Paul T. Wingfield; Wiley Interscience 1995-2003)"

Providing a cell includes the preparation, cultivation and further processing of the cell. Cells are provided, for example, by preparing suitable cell material from organs or tissues or by propagating suitable cell lines or microorganisms. Various suitable culture media can be used for cultivation. The cells are maintained at the optimum temperature for the organism. Where appropriate, preservatives, antibiotics, pH indicators, blood serum components, blood serum, auxiliaries or the other substances are added to the growth medium used in each case. Processes for preparation, cultivation and further processing are described in standard textbooks (Example: Basic Cell Culture; Ed. J. M. Davis; IRL Press; 1994).

The application of recombinant techniques provides e.g. for a construct to be expressed in a cell. Such a construct consisting of a polynucleotide sequence can be prepared by a skilled worker in a routine manner with the aid of his specialist knowledge. The worker skilled in molecular biology/biochemistry can find the specialist knowledge for this, for example, in "F. M. Ausubel et al.; Current Protocols in Molecular Biology; John Willey & Sons; New York". A vector construct for example is prepared by incorporating a polynucleotide coding for the amino acid sequence of, for example, a GPCR into an expression vector. An expression vector is a vector in which a polynucleotide sequence can be translated in a host cell into a protein. Vectors may be derived from plasmids, viruses or cosmids and must be capable of autonomous replication. They generally contain an origin of replication, cleavage sites for restriction enzymes and marker genes such as, for example, antibiotic resistance genes. In an expression vector, the polynucleotide sequence which is to be propagated or which has been introduced from the outside is under the functional control of a promoter. A promoter is a functional polynucleotide sequence of variable length, which is used to control transcription, i.e. synthesis of mRNA of a polynucleotide sequence immediately 3'-of said promoter. There are promoters which are active only in prokaryotes, such as, for example, the lac, tac and trc promoters, and also promoters which are active only in eucaryotes, such as, for example, CMV or ADH promoters. In a preferred embodiment, the recombinant vector construct comprises an expression vector usable in eucaryotes and/or procaryotes. An expression vector contains a promoter which can be linked functionally to a polynucleotide sequence so that a protein encoded by said polynucleotide sequence is synthesized in an organism, for example a bacterium, fungus or the cell of a eucaryotic cell line. The promoter may be inducible, e.g. by means of tryptophan, or may be constitutively active. Examples of expression vectors are pUC18, pUC19, pBluescript, pcDNA3.1.

Transfection is the introduction of foreign polynucleotide sequences into a host cell and the subsequent propagation of said polynucleotide sequence to any number of identical copies.

A cell line is transiently transfected with a recombinant construct by means of routine methods which can be found by the skilled worker in the above mentioned textbook "Current Protocols in Molecular Biology, published by John Wiley & Sons, New York", or in "Sambrook et al.; A Laboratory Manual, Cold Spring Harbor Laboratory, ISBN 0-87969-309-6". Examples of such routine methods are electroporation, $Ca^{2+}$-phosphate coprecipitation and transfection by means of liposomes. The transfected genes may be expressed in the host cell by Western blotting of cell lysates of transfected cells in combination with an immunological detection method. For this too, the required laboratory protocols can be found by the skilled worker in the manuals mentioned above. Specific antibodies for immunodetection of different GPCR receptors are commercially available.

A chemical compound is provided in particular by chemical synthesis or isolation of chemical substances from biological material.

The skilled worker may use routine methods for chemical synthesis of a compound or isolation of a substance from cell. Such methods are available to the skilled worker in textbooks such as "Organic Synthesis Workbook; 1995; John Wiley & Sons; ISBN 3-527-30187-9", "The Organic Chemistry of Drug Synthesis; 1998; John Wiley & Sons; ISBN 0-471-24510-0", or "Bioactive Compounds from Natural Sources; 2001; Taylor & Francis; ISBN 0-7484-0890-8".

The compounds obtained by synthesis or isolation may be dissolved in a suitable solvent. Suitable solvents may contain water, buffer substances (e.g. Tris, HEPES, MOPS, etc.], monovalent and/or divalent ions (e.g. $K^+$, $Na^+$, $Mg^{2+}$, $Ca^{2+}$, etc.], acids (e.g. HCl, $H_2SO_4$, formic acid, acetic acid, etc.], bases (e.g. NaOH, etc.], alcohol (e.g. methanol, ethanol, glycerol], detergents (e.g. Na dodecyl sulfate, etc.], organic solvents (e.g. formamide, acetone, dimethyl sulfoxide, etc.] and other components, in particular solubilizers and stabilizers.

The skilled worker is able to bring in contact the components of the assay of the invention by using laboratory routine methods. Contacting may take place, for example, in Erlenmeyer vessels, tubes, Eppendorf vessels or in microtiter plates. Temperature-controlled incubators for which a constant temperature of, for example, 30° C. or 37° C. and fixed $CO_2$ or humidity conditions can be set may be used for said contacting. Contacting may in particular also be carried out in laboratory robot devices. Contacting is possible for different periods of time, from a few seconds to minutes and up to several hours. The conditions to be chosen in each case depend on the receptor, the cell line and the chemical compound.

The final form of pharmaceutical relates to the final formulation, for example, as tablet, granules, spray, solution, ointment, tincture or other formulation forms.

Processing to the final form refers to the preparation of the particular formulation in generally, the daily dose is in the range from 0.3 mg to 100 mg (typically from 3 mg to 50 mg) per day and per Kilogram of body weight, for example, 3-10 mg/kg/day. An intravenous dose may be, for example, in the range from 0.3 mg to 1.0 mg/kg and can most suitably be administered as infusion of from 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active substance. It is thus possible for ampoules for injections to contain, for example, from 1 mg to 100 mg, and for single-dose formulations which can be administered orally, such as, for example, tablets or capsules, to contain, for example, from 1.0 to 1000 mg, typically from 10 to 600 mg.

EXAMPLES

Materials and methods with respect to the forthcoming experimental protocols have been summarized in tables 1, 2 and 3.

Identification of AlphaScreen Artifacts:

Compounds: 100 µM in Test Buffer A

Detection solution: anti-streptavidin antibody (1:833], streptavidin donor beads (20 µg/ml], protein-A acceptor beads (40 µg/ml] in a buffer mixed from 1 part test buffer A containing the kinase, 2 test buffer A containing the kinase substrates and 2 parts test buffer B containing the phospho-specific antibody    1 µl compound    +5 µl detection solution    seal the plate, incubate overnight at room temperature    read the plate in the Alpha Quest Dilution of Compounds:

(1) For single concentration screening:

dilute 1 µl compound (10 mM in dimethylsulfoxide) with 100 µM test buffer A (2) For dose-response measurements:

5 µl 10 mM in DMSO (Dimethylsulfoxide]

+120 µl 20 mM Tris-HCl, pH 7.4, 20 mM $MgCl_2$, 4 mM EDTA, 0.2% BSA, 5% DMSO (400 µM, corresponds to 100 µM in enzymatic reaction)

serial 1+1 dilution (40+40 µl] in 20 mM Tris-HCl, pH 7.4, 20 mM $MgCl_2$, 4 mM EDTA, 0.2% BSA, 9% DMSO, 7 dilutions (overall concentration range 400-3.125 µM, [DMSO]=9% at all compound concentrations]

Reaction:

1 µl compound

+1 µl reaction mix A without DMSO ([DMSO]=2.25% during reaction)

+2 µl ATP, incubate for 120 min at room temperature

+2 µl stop/detection solution, seal the plate, incubate over night at room temperature    read the plate Data Analysis Calculation of Percent-Inhibition Values    Percent-inhibition values are calculated as:

$$\% \text{ inhibition} = 100 \cdot \left( \frac{\text{value} - \text{low control}}{\text{high control} - \text{low control}} \right)$$

read the plate in the Alpha Quest (a HTS microplate analyzer)

Assay quality parameters were determined on the basis of high and low controls, which were run as internal standards on each assay plate. The following quality parameters are used as a measure to judge the suitability of an assay for high throughput screening.

Signal to Background (S/B]

$$S/B = \frac{mean_{high\ control}}{mean_{low\ control}}$$

Z'-Factor $$Z' = 1 - \frac{(3 * SD_{high\ control} + 3 * SD_{low\ control}]}{|mean_{high\ control} - mean_{low\ control}|}$$

Identification of Positives

Wells with % inhibition values larger than (mean+3σ] were considered as positives.

Purification of GRK

Several methods for purification of GRK are available from the state of the art. In "Söhlemann et al., 1993, FEBS Lett. 324, 59-62" the purification and functional characterization of β-adrenergic receptor kinase after having expressed the kinase in insect cells was described.

Furthermore, "Kim et al., 1993, Receptor 3, 39-55" described expression and characterization of two β-adrenergic receptor kinase isoforms in a baculovirus expression system.

Manufacturing of Antibodies

The construction of hybridoma cell lines producing monoclonal antibodies against different GRK derived peptides has been described in amongst others "Martin Oppermann et al., 1999, Journal of Biol. 274, 8875-8895".

Manufacturing of murine monoclonal antibody in particular of E11/19 (or others as R22/7, T21/2) which either binds to a CCR5 N-terminal epitope and in particular to an peptide having an amino acid sequence according to SEQ ID NO. 1 was described in "Pollok-Kopp et al., J. Biol. Chem. 2003, 278, 2190-2198".

Description of Tables
Table 1: Stock solutions
Table 2: Buffers and reagents
Table 3: Reagent Concentrations in the assay
Table 4: Summary of results of the primary screen of two test sets

TABLE 1

| name | composition | preparation | storage |
|---|---|---|---|
| Tris buffer A | 20 mM, pH 7.4 | dissolve 2.4 g Tris in H$_2$O, adjust pH with HCl, make up to 1 l with H$_2$O | room temperature |
| Tris buffer B | 10 mM, pH 7.4 | dissolve 1.2 g Tris in H$_2$O, adjust pH with HCl, make up to 1 l with H$_2$O | room temperature |
| EDTA_A | 0.5 M, pH 7.4 | dissolve 190 g EDTA in H$_2$O, adjust pH to 7.4 with NaOH, make up to 1 l with H$_2$O | 4° C. |
| EDTA_B | 0.5 M, pH 7.8 | dissolve 190 g EDTA in H$_2$O, adjust pH to 7.8 with NaOH, make up to 1 l with H$_2$O | 4° C. |
| BSA | 10% | dissolve 100 g BSA in 1 l H$_2$O | −20° C. |
| ATP | 400 μM | dissolve 220 mg ATP in 1 l H$_2$O | −20° C. |
| MgCl$_2$ | 2.4 M | add 228 g MgCl$_2$ to 1 l H$_2$O | 4° C. |
| CCR5 peptide | 350 μM in DMSO | dissolve 0.98 mg in 1 ml DMSO | −20° C. |
| CCR5 peptide | 3.5 μM in Tris buffer A | dilute CCR5 DMSO stock 1:100 in Tris buffer A | −20° C. (aliquots] |
| βARK | 12.9 mg/ml (162 μM] | use as provided by protein production | −80° C. |
| Anti-CCR5 | 1.22 mg/ml (7.4 μM] | use as provided by Martin Oppermann (University of Gottingen] | 4° C. |
| Heparin | 300 μM | provided by J. Huber, prepared by dissolving 5.1 mg in 1 ml 20 mM Hepes-KOH, pH 7.4, 2 mM EDTA, 1% DMSO | −20° C. |
| wash solution A | 10% ethanol | mix 100 ml ethanol and 900 ml Tris buffer A | room temperature |
| wash solution B | 10% ethanol, 0.001% pluronic | mix 100 ml ethanol, 900 ml H$_2$O and 0.1 ml 10% Pluronic F-68 | room temperature |

TABLE 2

| name | preparation | stability |
|---|---|---|
| test buffer A | 1 liter: 932 ml Tris buffer A, 8 ml EDTA_A, 20 ml BSA, 40 ml DMSO | one day |
| test buffer B | 1 liter: 986 ml Tris buffer B, 4 ml EDTA_A, 10 ml BSA | one day |
| compounds | add 100 μl test buffer A to 1 μl compound | one day |
| heparin | dilute 1 μl 300 μM stock in 749 μl test buffer A | one day |
| reaction mix A | 3 ml: 345 μl CCR5 peptide (3.5 μM], 37 μl □□RK, 50 μl MgCl$_2$, 2568 μl test buffer A | 60 min |
| reaction mix B | 3 ml: 345 μl CCR5 peptide (3.5 μM], 50 μl MgCl$_2$, 2568 μl test buffer A | 60 min |
| ATP | dilute stock 1:20 in H$_2$O | one day |
| stop/ detection solution | 5 ml: 4061 μl test buffer B, 60.2 μl donor beads (5 mg/ml], 120.5 μl acceptor beads (5 mg/ml], 150 μl BSA, 600 μl EDTA_B, 8.1 μl anti-pCCR5 | 60 min (store in the dark] |

TABLE 3

| component | concentration during reaction | concentration during detection |
|---|---|---|
| buffer | 10 mM Tris-HCl, 10 mM MgCl$_2$, 2 mM EDTA, 0.1% BSA, pH 7.4 | 10 mM Tris-HCl, 10 mM MgCl$_2$, 22 mM EDTA, 0.1% BSA, pH 7.8 |
| DMSO | 2.25% | 1.125% |
| □ARK | 0.5 μM | 0.33 μM |
| CCR5 peptide | 100 nM | 67 nM |
| ATP | 10 μM | 6.7 μM |
| anti-pCCR5 | — | 4 nM |
| donor beads | — | 20 μg/ml |
| acceptor beads | — | 40 μg/ml |

TABLE 4

| Test set | 020813 | 020819 |
|---|---|---|
| [compound]/μM | 25 | 25 |
| No. of plates | 48 | 55 |
| No. of compounds | 16255 | 18592 |
| mean % inhibition ± SD* | 15 ± 15.4 | 10 ± 13.5 |
| Threshold for positives (% inhibition]** | 50 | 40 |
| Number of positives | 764 | 765 |
| Number of reordered compounds*** | 1124 | 1071 |
| S/B (avg. per plate] | 1.60 ± 0.04 | 2.31 ± 0.09 |
| Z-factor (avg. per plate ± SD] | 0.06 ± 0.22 | 0.43 ± 0.15 |
| Z'-factor (avg. per plate ± SD] | 0.74 ± 0.07 | 0.85 ± 0.06 |

*for wells between −50 and +100% inhibition (>98.9% of all data], after correction for border effects

**Due to the relatively small S/B, the threshold for positives was lowered by 10% compared to the threshold determined as mean +3☐.

***In addition to the positives, all compounds at well positions with >5 positives (see FIG. 8] were also re-ordered for confirmation.

---

The invention claimed is:

1. A method for detecting the phosphorylation of a substrate molecule by a protein kinase comprising the steps of:
   a] providing at least one protein kinase,
   b] providing at least one substrate molecule of said protein kinase wherein said substrate molecule consists of a peptide consisting of amino acid sequence SEQ ID NO: 1,
   c] proving at least one donor component which is able to bind to said substrate molecule and which emits a signal after said donor component is irradiated by a light source,
   d] providing at least one acceptor component which is able to bind to said substrate molecule if said substrate has been phosphorylated and is able to receive a signal from said donor component and emit the signal in the form of an electromagnetic radiation,
   e] bringing said protein kinase, said substrate molecule, said donor component and said acceptor component in contact with each other,
   f] irradiating the mixture of step e] with a light source in such a way that said donor component is excited and,
   g] measuring the electromagnetic radiation which is emitted by said mixture.

2. The method of claim 1 wherein said substrate molecule is linked to an antibody which is able to bind to said donor component.

3. The method of claim 1 wherein said donor component is linked to an antibody which is able to bind to said substrate molecule.

4. The method of claim 1 wherein said substrate molecule is linked to a first antibody and said donor component is linked to a second antibody. and wherein either the first antibody is able to bind to the second antibody or the second antibody is able to bind to the first antibody.

5. The method of claim 1 wherein said substrate molecule is linked to a biotin molecule and said donor component is linked to streptavidin.

6. The method of claim 1 wherein said substrate molecule is linked to streptavidin and said donor component is linked to biotin.

7. The method of claim 1 wherein said protein kinase is selected from the group consisting of beta-adrenergic-receptor-kinase 1 and G-protein-coupled-receptor-kinase 2.

8. The method of claim 1 wherein said electromagnetic radiation is fluorescence radiation.

9. The method of claim 1 wherein said light source is selected from the group consisting of a laser and a lamp.

10. The method of claim wherein the signal is transferred from said donor component to said acceptor component by emissionless energy transfer.

11. The method of claim 10 wherein said emissionless energy transfer is fluorescence resonance energy transfer.

12. The method of claim 1 wherein said acceptor component comprises at least one antibody that specifically recognizes said substrate molecule when it is phosphorylated or said acceptor component has the capacity to bind to at least one antibody which specifically recognizes said substrate molecule when said substrate molecule is phosphorylated.

13. The method of claim 12 wherein said antibody that is part of or binding to said acceptor component is the monoclonal antibody E11/19.

14. The method of claim 1 wherein the signal is transferred from said donor component to said acceptor component via singlet oxygen wherein said donor component comprises a compound which is able to convert triplet oxygen to singlet oxygen after excitation by a laser and wherein said acceptor component comprises at least one first compound excitable by singlet oxygen and at least one second compound capable of absorbing in an emissionless manner arid emitting in the form of fluorescence radiation the energy absorbed by the first compound.

15. The method of claim 14 wherein said donor component and said acceptor component consists of particles on which donor groups or acceptor groups are localized.

16. The method of claim 15 wherein said particles have an average diameter of approximately 200 nm.

17. The method of claim 1 comprising the additional step of adding at least one test substance and observing the influence of said test substance on the activity of said protein kinase.

18. A peptide consisting of an amino acid sequence of Seq ID No. 1.

19. The peptide according to claim 18 wherein the peptide is biotinylated.

* * * * *

SEQUENCE LISTING

<160> NUMBER OF SEQ ID NOS: 2

<210> SEQ ID NO 1
<211> LENGTH: 22
<212> TYPE: PRT
<213> ORGANISM: Homo sapiens

<400> SEQUENCE: 1

Ala Pro Glu Arg Ala Ser Ser Val Tyr Thr Arg Ser Thr Gly Glu Gln
1               5                   10                  15

Glu Ile Ser Val Gly Leu
            20

<210> SEQ ID NO 2
<211> LENGTH: 689
<212> TYPE: PRT
<213> ORGANISM: Homo sapiens

<400> SEQUENCE: 2

Met Ala Asp Leu Glu Ala Val Leu Ala Asp Val Ser Tyr Leu Met Ala
1               5                   10                  15

Met Glu Lys Ser Lys Ala Thr Pro Ala Ala Arg Ala Ser Lys Lys Ile
            20                  25                  30

Leu Leu Pro Glu Pro Ser Ile Arg Ser Val Met Gln Lys Tyr Leu Glu
        35                  40                  45

Asp Arg Gly Glu Val Thr Phe Glu Lys Ile Phe Ser Gln Lys Leu Gly
    50                  55                  60

Tyr Leu Leu Phe Arg Asp Phe Cys Leu Asn His Leu Glu Glu Ala Arg
65                  70                  75                  80

Pro Leu Val Glu Phe Tyr Glu Glu Ile Lys Lys Tyr Glu Lys Leu Glu
                85                  90                  95

Thr Glu Glu Glu Arg Val Ala Arg Ser Arg Glu Ile Phe Asp Ser Tyr
            100                 105                 110

Ile Met Lys Glu Leu Leu Ala Cys Ser His Pro Phe Ser Lys Ser Ala
        115                 120                 125

Thr Glu His Val Gln Gly His Leu Gly Lys Lys Gln Val Pro Pro Asp
    130                 135                 140

Leu Phe Gln Pro Tyr Ile Glu Glu Ile Cys Gln Asn Leu Arg Gly Asp
145                 150                 155                 160

Val Phe Gln Lys Phe Ile Glu Ser Asp Lys Phe Thr Arg Phe Cys Gln
                165                 170                 175

-continued

```
Trp Lys Asn Val Glu Leu Asn Ile His Leu Thr Met Asn Asp Phe Ser
            180                 185                 190

Val His Arg Ile Ile Gly Arg Gly Phe Gly Glu Val Tyr Gly Cys
        195                 200                 205

Arg Lys Arg Asp Thr Gly Lys Met Tyr Ala Met Lys Cys Leu Asp Lys
        210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255

Met Ser Tyr Ala Phe His Thr Pro Asp Lys Leu Ser Phe Ile Leu Asp
            260                 265                 270

Leu Met Asn Gly Gly Asp Leu His Tyr His Leu Ser Gln His Gly Val
            275                 280                 285

Phe Ser Glu Ala Asp Met Arg Phe Tyr Ala Ala Glu Ile Ile Leu Gly
        290                 295                 300

Leu Glu His Met His Asn Arg Phe Val Val Tyr Arg Asp Leu Lys Pro
305                 310                 315                 320

Ala Asn Ile Leu Leu Asp Glu His Gly His Val Arg Ile Ser Asp Leu
                325                 330                 335

Gly Leu Ala Cys Asp Phe Ser Lys Lys Lys Pro His Ala Ser Val Gly
            340                 345                 350

Thr His Gly Tyr Met Ala Pro Glu Val Leu Gln Lys Gly Val Ala Tyr
        355                 360                 365

Asp Ser Ser Ala Asp Trp Phe Ser Leu Gly Cys Met Leu Phe Lys Leu
        370                 375                 380

Leu Arg Gly His Ser Pro Phe Arg Gln His Lys Thr Lys Asp Lys His
385                 390                 395                 400

Glu Ile Asp Arg Met Thr Leu Thr Met Ala Val Glu Leu Pro Asp Ser
                405                 410                 415

Phe Ser Pro Glu Leu His Ser Leu Leu Glu Gly Leu Leu Gln Arg Asp
            420                 425                 430

Val Asn Arg Arg Leu Gly Cys Leu Gly Arg Gly Ala Gln Glu Val Lys
        435                 440                 445

Glu Ser Pro Phe Phe Arg Ser Leu Asp Trp Gln Met Val Phe Leu Gln
        450                 455                 460

Arg Tyr Pro Pro Pro Leu Ile Pro Pro Arg Gly Glu Val Asn Ala Ala
465                 470                 475                 480

Asp Ala Phe Asp Ile Gly Ser Phe Asp Glu Glu Asp Thr Lys Gly Ile
                485                 490                 495

Lys Leu Leu Asp Ser Asp Gln Glu Leu Tyr Arg Asn Phe Pro Leu Thr
            500                 505                 510

Ile Ser Glu Arg Trp Gln Gln Glu Val Ala Glu Thr Val Phe Asp Thr
        515                 520                 525

Ile Asn Ala Glu Thr Asp Arg Leu Glu Ala Arg Lys Lys Ala Lys Asn
        530                 535                 540

Lys Gln Leu Gly His Glu Glu Asp Tyr Ala Leu Gly Lys Asp Cys Ile
545                 550                 555                 560

Met His Gly Tyr Met Ser Lys Met Gly Asn Pro Phe Leu Thr Gln Trp
                565                 570                 575

Gln Arg Arg Tyr Phe Tyr Leu Phe Pro Asn Arg Leu Glu Trp Arg Gly
            580                 585                 590

Glu Gly Glu Ala Pro Gln Ser Leu Leu Thr Met Glu Glu Ile Gln Ser
```

-continued

```
                595                 600                 605
Val Glu Glu Thr Gln Ile Lys Glu Arg Lys Cys Leu Leu Leu Lys Ile
    610                 615                 620

Arg Gly Gly Lys Gln Phe Ile Leu Gln Cys Asp Ser Asp Pro Glu Leu
625                 630                 635                 640

Val Gln Trp Lys Lys Glu Leu Arg Asp Ala Tyr Arg Glu Ala Gln Gln
                645                 650                 655

Leu Val Gln Arg Val Pro Lys Met Lys Asn Lys Pro Arg Ser Pro Val
            660                 665                 670

Val Glu Leu Ser Lys Val Pro Leu Val Gln Arg Gly Ser Ala Asn Gly
        675                 680                 685

Leu
```